(12) United States Patent
Lee et al.

(10) Patent No.: US 8,574,433 B2
(45) Date of Patent: **\*Nov. 5, 2013**

(54) ION EXCHANGE POROUS RESINS FOR SOLID PHASE EXTRACTION AND CHROMATOGRAPHY

(75) Inventors: Peter Jeng-Jong Lee, Westborough, MA (US); John E. O'Gara, Ashland, MA (US)

(73) Assignee: Waters Technologies Corporation, Milford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/855,300

(22) Filed: Aug. 12, 2010

(65) Prior Publication Data

US 2010/0324159 A1    Dec. 23, 2010

Related U.S. Application Data

(60) Division of application No. 12/259,199, filed on Oct. 27, 2008, now Pat. No. 7,790,038, which is a continuation of application No. 11/799,376, filed on May 1, 2007, now Pat. No. 7,442,299, which is a division of application No. 10/169,546, filed as application No. PCT/US99/13241 on Jun. 10, 1999, now Pat. No. 7,232,520.

(60) Provisional application No. 60/089,153, filed on Jun. 12, 1998.

(51) Int. Cl.
*B01D 15/08* (2006.01)

(52) U.S. Cl.
USPC ............ 210/198.2; 210/502.1; 210/635; 210/656; 502/402

(58) Field of Classification Search
USPC ............ 210/634, 635, 656, 198.2, 502.1; 96/101; 502/402; 521/32, 33; 525/326.9, 330.3, 330.4, 330.5
See application file for complete search history.

(56) References Cited

U.S. PATENT DOCUMENTS

| 2,540,985 | A | * | 2/1951 | Jackson ..................... 521/31 |
| 2,788,331 | A | | 4/1957 | Greer et al. |
| 2,801,224 | A | | 7/1957 | Greer |
| 2,824,844 | A | | 2/1958 | Gilwood |
| 3,499,960 | A | | 3/1970 | Stauffer et al. |
| 3,816,355 | A | | 6/1974 | Clemens |
| 3,946,749 | A | | 3/1976 | Papantoniou et al. |
| 3,954,682 | A | | 5/1976 | Fein et al. |

(Continued)

FOREIGN PATENT DOCUMENTS

EP          0852334          7/1998

OTHER PUBLICATIONS

J. Lieto, et al.; "Polymer supports for catalysts"; Chemtech.; pp. 46-53; (1983).

(Continued)

*Primary Examiner* — Ernest G Therkorn
(74) *Attorney, Agent, or Firm* — Edwards Wildman Palmer LLP; Mark D. Russett

(57) ABSTRACT

Embodiments of the present invention are directed to porous resins for solid phase extractions. The resins feature at least one hydrophobic component, at least one hydrophilic component and at least one ion exchange functional group. The resins exhibit superior wetting and ion exchange performance.

12 Claims, 8 Drawing Sheets

(56) References Cited

U.S. PATENT DOCUMENTS

| | | | |
|---|---|---|---|
| 3,985,540 A | 10/1976 | Fein et al. | |
| 3,991,018 A | 11/1976 | Strop et al. | |
| 4,000,098 A | 12/1976 | Hofstee | |
| 4,101,461 A | 7/1978 | Strop et al. | |
| 4,192,921 A | 3/1980 | Dales | |
| 4,297,220 A * | 10/1981 | Meitzner et al. | 210/690 |
| 4,303,531 A * | 12/1981 | Kawabata et al. | 210/663 |
| 4,468,330 A * | 8/1984 | Kamiyama et al. | 210/656 |
| 4,523,959 A * | 6/1985 | Exertier | 127/46.2 |
| 4,622,288 A * | 11/1986 | Yokoyama et al. | 430/527 |
| 4,711,863 A * | 12/1987 | Streat et al. | 502/5 |
| 4,758,413 A | 7/1988 | Harris et al. | |
| 4,789,479 A * | 12/1988 | Onitsuka et al. | 210/635 |
| 4,828,710 A | 5/1989 | Itoh et al. | |
| 4,889,632 A | 12/1989 | Svec et al. | |
| 4,923,610 A | 5/1990 | Svec et al. | |
| 4,933,372 A | 6/1990 | Feibush et al. | |
| 4,952,349 A | 8/1990 | Svec et al. | |
| 4,954,262 A * | 9/1990 | Aoki et al. | 210/638 |
| 5,030,352 A | 7/1991 | Varady et al. | |
| 5,230,806 A | 7/1993 | Fritz et al. | |
| 5,238,992 A * | 8/1993 | Outubuddin | 524/710 |
| 5,278,339 A * | 1/1994 | Cook | 562/509 |
| 5,292,818 A | 3/1994 | Oishi et al. | |
| 5,292,828 A * | 3/1994 | Jenkins et al. | 525/420 |
| 5,431,807 A * | 7/1995 | Frechet et al. | 210/198.2 |
| 5,453,185 A | 9/1995 | Frechet et al. | |
| 5,587,323 A | 12/1996 | Lewis et al. | |
| 5,618,438 A | 4/1997 | Fritz et al. | |
| 5,728,457 A | 3/1998 | Frechet et al. | |
| 5,840,911 A | 11/1998 | Frei et al. | |
| 5,882,521 A | 3/1999 | Bouvier et al. | |
| 5,976,367 A | 11/1999 | Bouvier et al. | |
| 6,045,697 A | 4/2000 | Girot et al. | |
| 6,106,721 A | 8/2000 | Bouvier et al. | |
| 6,117,996 A | 9/2000 | Lowe et al. | |
| 6,238,565 B1 | 5/2001 | Hatch | |
| 6,248,798 B1 | 6/2001 | Slingsby et al. | |
| 6,322,695 B1 * | 11/2001 | Lee et al. | 210/198.2 |
| 6,362,245 B1 | 3/2002 | Takahashi et al. | |
| 6,686,035 B2 | 2/2004 | Jiang et al. | |
| 6,946,070 B2 | 9/2005 | Hammen et al. | |
| 7,232,520 B1 | 6/2007 | Lee et al. | |
| 7,442,299 B2 | 10/2008 | Lee et al. | |
| 2002/0004561 A1 | 1/2002 | Takahashi et al. | |
| 2002/0043499 A1 | 4/2002 | Hammen et al. | |
| 2006/0021939 A1 | 2/2006 | Mallet et al. | |
| 2007/0205156 A1 | 9/2007 | Lee et al. | |

OTHER PUBLICATIONS

A. R. Mitchell, et al.; "Preparation of aminomethyl-polystyrene resin by direct amidomethylation"; Tetrahedron Letters; 42; pp. 3795-3798; (1976).

K. Unger; "Packings and stationary phases in chromatographic techniques"; Chromatographic Science Series; 47; pp. 585-720 (1990).

M. S. Mills, et al.; "Application of mixed-mode, solid-phase extraction in environmental and clinical chemistry"; Journal of Chromatography; 629; pp. 11-21; (1993).

http://en.wikipedia.org/wilki/Amide Nov. 15, 2007.

* cited by examiner

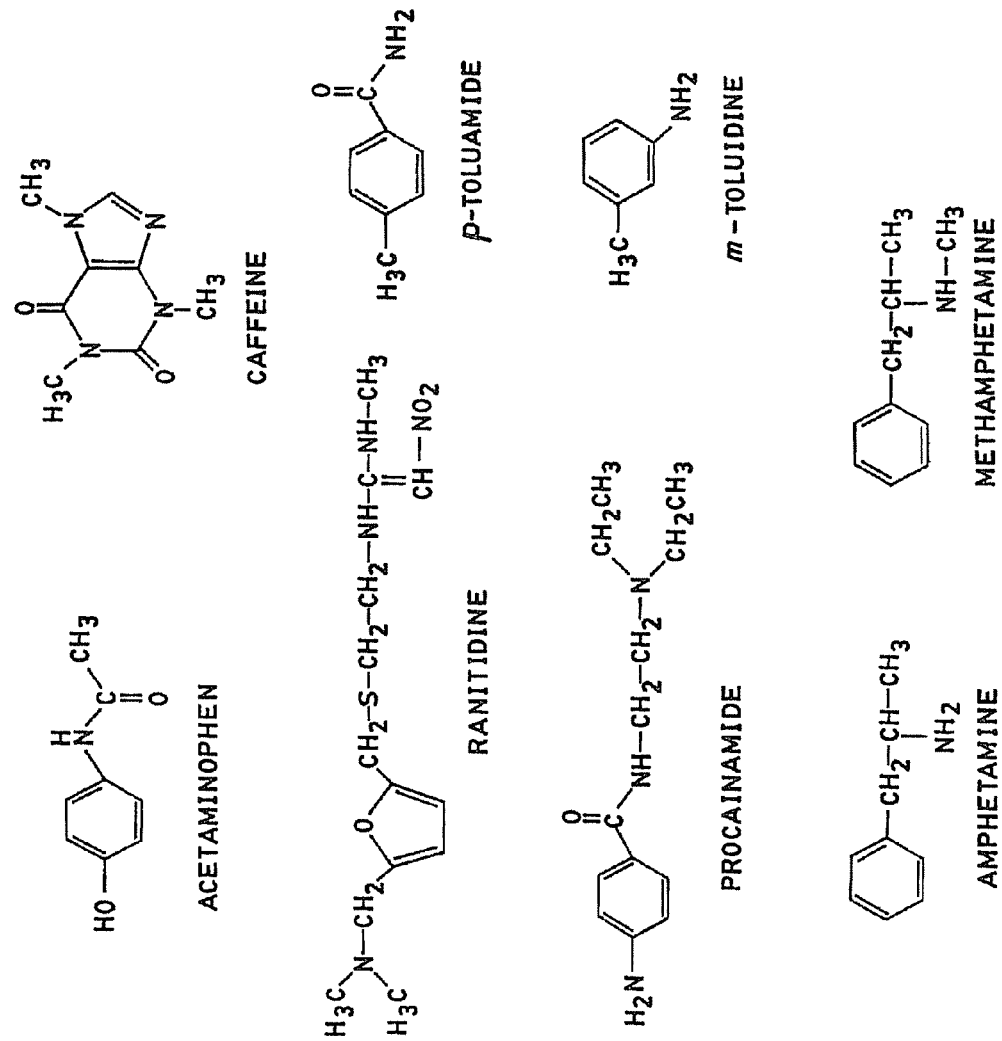

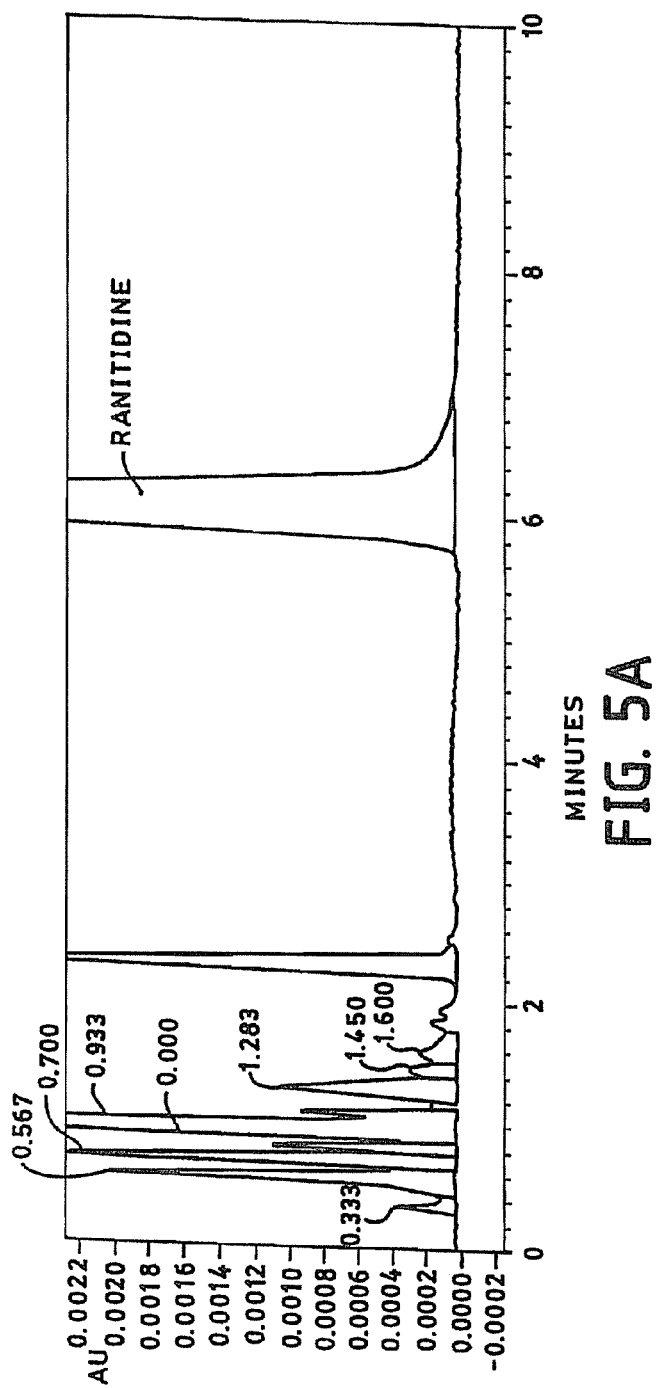

ION EXCHANGE POROUS RESINS FOR SOLID PHASE EXTRACTION AND CHROMATOGRAPHY

CROSS REFERENCE TO RELATED APPLICATIONS

This application is a divisional of application Ser. No. 12/259,199 filed Oct. 27, 2008, now U.S. Pat. No. 7,790,038, which is a continuation of application Ser. No. 11/799,376, filed May 1, 2007, now U.S. Pat. No. 7,442,299, which is a divisional of application Ser. No. 10/169,546, filed Jan. 16, 2003, now U.S. Pat. No. 7,232,520, which is the U.S. national phase application, pursuant to 35 U.S.C. §371, of PCT international application Ser. No. PCT/US99/13241, filed Jun. 10, 1999, designating the United States and published in English on Dec. 16, 1999 as publication no. WO 99/64480, which claims priority to U.S. provisional application Ser. No. 60/089,153, filed Jun. 12, 1998. The entire contents of the aforementioned patent applications are incorporated herein by this reference.

FIELD OF THE INVENTION

This invention relates generally to novel porous resins for solid phase extraction and chromatography which contain at least one hydrophobic component, at least one hydrophilic component and at least one ion exchange functional group.

BACKGROUND OF THE INVENTION

Solid phase extraction (SPE) is a chromatographic technique which is widely used, e.g., for preconcentration and cleanup of analytical samples, for purification of various chemicals, and for removal of toxic or valuable substances from aqueous solutions. SPE is usually performed using a column or cartridge containing an appropriate resin. SPE procedures have been developed using sorbents which can interact with analytes by hydrophobic, ion exchange, chelation, sorption, and other mechanisms, to bind and remove the analytes from fluids. Since different SPE applications can require different sorbents, there is a need for sorbents with novel properties which have unique selectivities.

SUMMARY OF THE INVENTION

It is an object of the invention to provide compounds which can be used as porous resins for solid phase extraction and chromatography which exhibit superior wetting characteristics.

It is yet another object of the invention to provide porous resin compounds which have unique selectivities. porous resin compounds which can selectively capture analytes of interest and allow interfering analytes to pass through unretained.

It is yet another object of the invention to provide porous resin compounds having an ion exchange functional group, a hydrophobic component and a hydrophilic polar component.

It is yet another object of the invention to utilize the novel porous resins of this invention to isolate or remove a solute from a solution.

Still another object of the invention is to utilize the novel porous resins of this invention to analytically determine the level of a solute in a solution.

In one aspect, the invention features a compound of the formula:

and salts thereof, wherein the order of A, B and C may be random, block, or a combination of random and block;

wherein $$\frac{1}{100} < \frac{(p+n)}{m} < \frac{100}{1}$$

and $$\frac{1}{500} < \frac{p}{n} < \frac{100}{1}$$

wherein A is selected from the group consisting of

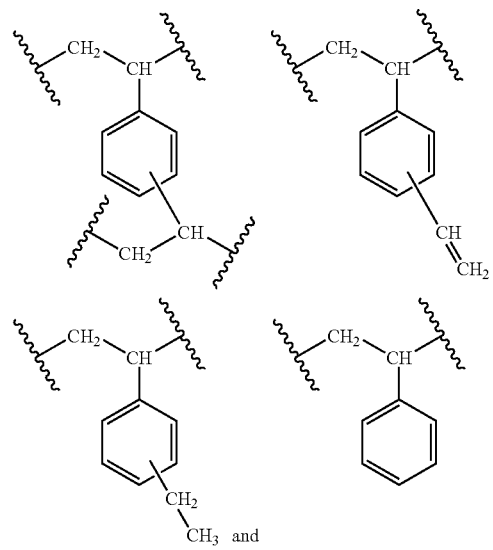

wherein B is selected from the group consisting of

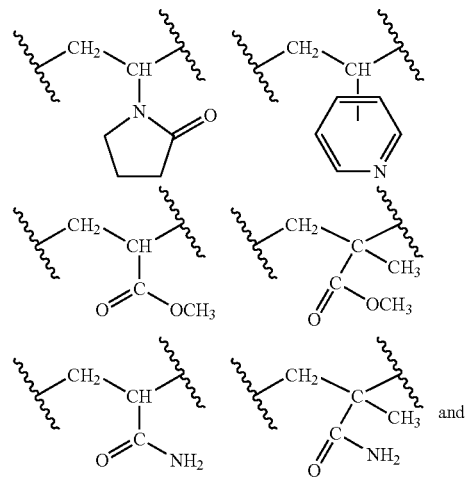

-continued

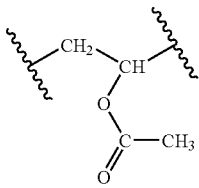

wherein C is A or modified A, wherein modified A is selected from the group consisting of

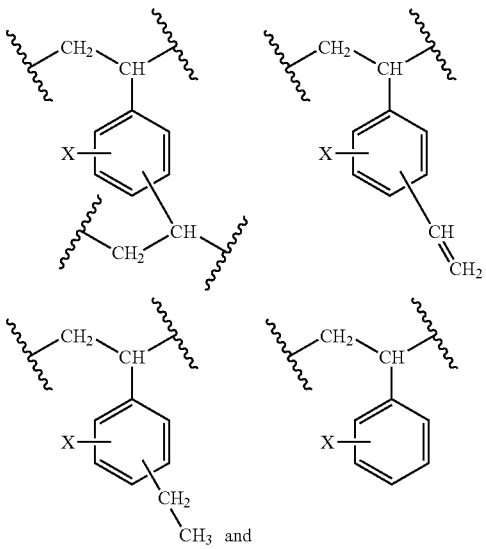

wherein X is selected from the group consisting of $SO_3H$, $CH_2CO_2H$, $CH_2CH(CO_2H)_2$, $CO_2H$, $PO_3H_2$, $PO_2H_2$, $CH_2PO_3H_2$, $CH_2Cl$, $CH_2NH_2$, $CH_2N[(CH_2)_yCH_3]_2$ wherein y is any integer from 0 to 18, $CH_2N^+[(CH_2)_{y=}CH_3]_3D^-$ wherein y= is any integer from 0 to 18 and $D^-$ is an anion, $SO_2NHR$ wherein R is polyethylenimine, and $CH_2NHR$ wherein R is polyethylenimine.

Another aspect of the invention is a porous resin formed by copolymerizing at least one hydrophobic monomer and at least one hydrophilic monomer so as to form a copolymer, and subjecting the copolymer to a sulfonation reaction so as to form a sulfonated copolymer comprising at least one ion-exchange functional group, at least one hydrophilic component and at least one hydrophobic component.

In preferred embodiments, the hydrophobic monomer is divinylbenzene, the hydrophilic monomer is N-vinylpyrrolidone, and the copolymer is a poly(divinylbenzene-co-N-vinylpyrrolidone). Preferably, the porous resin is a sulfonated poly(divinylbenzene-co-N-vinylpyrrolidone).

Another aspect of the invention is a porous resin for solid phase extraction or chromatography comprising at least one ion-exchange functional group, at least one hydrophilic component and at least one hydrophobic component.

Another aspect of the invention is a method for treating a solution to isolate or remove a solute. A solution having a solute is contacted with a porous resin under conditions so as to allow sorption of the solute to the porous resin. The porous resin comprises at least one ion-exchange functional group, at least one hydrophilic polar component and at least one hydrophobic component. In certain embodiments, the solute is removed from the porous resin. In certain embodiments, the ion-exchange functional group is $SO_3H$, $CH_2CO_2H$, $CH_2CH(CO_2H)_2$, $CO_2H$, $PO_3H_2$, $PO_2H_2$, $CH_2PO_3H_2$, $CH_2Cl$, $CH_2NH_2$, $CH_2N[(CH_2)_yCH_3]_2$ wherein y is any integer from 0 to 18, $CH_2N^+[(CH_2)_{y=}CH_3]_3D^-$ wherein y= is any integer from 0 to 18 and $D^-$ is an anion, $SO_2HMR$ wherein R is polyethylenimine, or $CH_2NHR$ wherein R is polyethylenimine. In certain embodiments, the hydrophilic monomer comprises a heterocyclic group, e.g., a saturated, unsaturated or aromatic heterocyclic group. Examples include nitrogen-containing heterocyclic groups, e.g., a pyridyl group, e.g., 2-vinylpyridine, 3-vinylpyridine or 4-vinylpyridine, or a pyrrolidonyl group, e.g., N-vinylpyrrolidone. In certain embodiments, the hydrophobic monomer comprises an aromatic carbocyclic group, e.g., a phenyl group or a phenylene group, or a straight chain $C_2$-$C_{18}$-alkyl group or a branched chain $C_2$-$C_{18}$-alkyl group. The hydrophobic monomer can be, e.g., styrene or divinylbenzene. A preferred copolymer is a poly(divinylbenzene-co-N-vinylpyrrolidone). A preferred porous resin is a compound of formula I and salts thereof. Preferably, the porous resin is a sulfonated poly(divinylbenzene-co-N-vinylpyrrolidone).

Another aspect of the invention is a method for analytically determining the level of solute in a solution. A solution having a solute is contacted with a porous resin under conditions so as to allow sorption of the solute to the porous resin. The resin comprises at least one ion-exchange functional group, at least one hydrophilic polar component and at least one hydrophobic component. The porous resin having the sorbed solute is washed with a solvent under conditions so as to desorb the solute from the porous resin. The level of the desorbed solute present in the solvent after the washing is analytically determined. In certain embodiments, the porous resin is a compound of formula I and salts thereof. Preferably, the porous resin is a sulfonated poly(divinylbenzene-co-N-vinylpyrrolidone).

Another aspect of the invention is a solid phase extraction cartridge comprising a porous resin packed inside an open-ended container. The porous resin comprises at least one ion-exchange functional group, at least one hydrophilic polar component and at least one hydrophobic component. In certain embodiments, the porous resin is a compound of formula I and salts thereof. Preferably, the porous resin is a sulfonated poly(divinylbenzene-co-N-vinylpyrrolidone).

The above and other features, objects and advantages of the present invention will be better understood by a reading of the following specification in conjunction with the drawings.

BRIEF DESCRIPTION OF THE DRAWINGS

FIG. 1 depicts the formulas of the model compounds acetaminophen, p-toluamide, caffeine, procainamide, ranitidine, amphetamine, methamphetamine and m-toluidine.

FIGS. 5A and 5B are chromatograms of methanol/ammonium hydroxide extract from porcine plasma using sulfonated poly(divinylbenzene-co-N-vinylpyrrolidone), Batch JJL03-

Figure 2A:
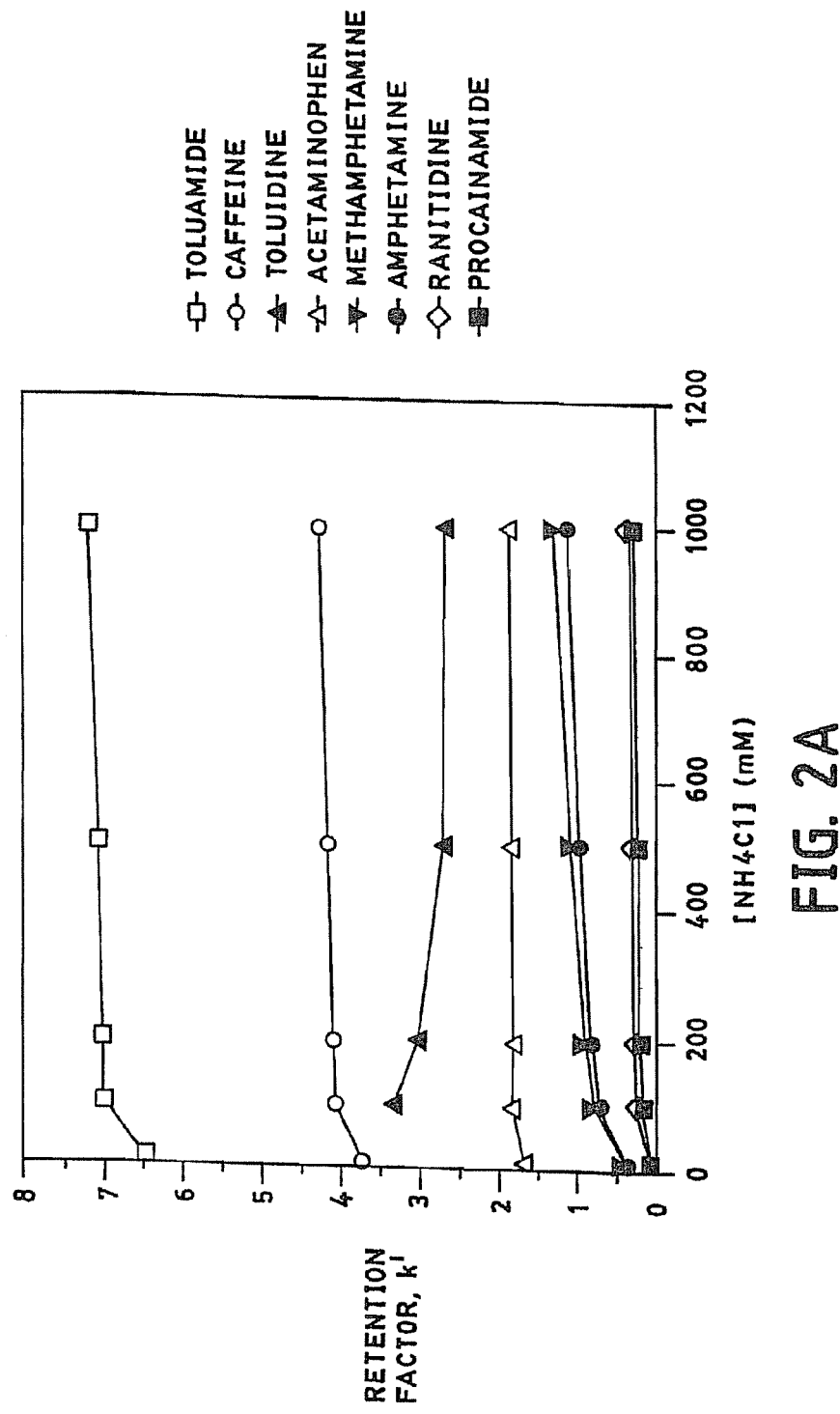
FIG. 2A is a graph depicting the effect of ionic strength on chromatographic retention for poly(divinylbenzene-co-N-vinylpyrrolidone), Batch 6B.

124 and Batch JJL03-100, for solid phase extraction, where ranitidine is an internal standard.

DETAILED DESCRIPTION

This invention provides for a compound of the formula:

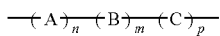
(I)

and salts thereof,
wherein the order of A, B and C may be random, block, or a combination of random and block;
wherein $$\frac{1}{100} < \frac{(p+n)}{m} < \frac{100}{1}$$

and $$\frac{1}{500} < \frac{p}{n} < \frac{100}{1}$$

wherein A is selected from the group consisting of

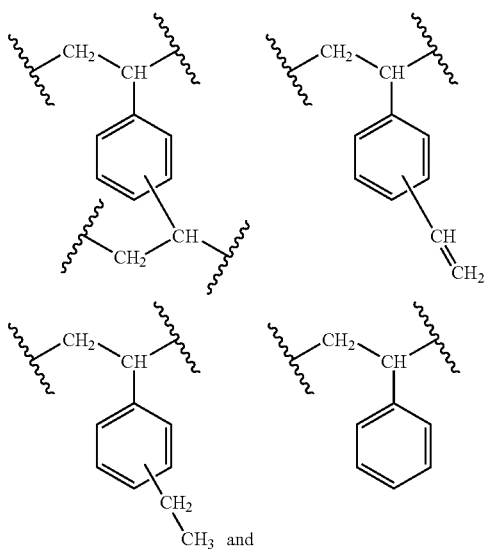

wherein B is selected from the group consisting of

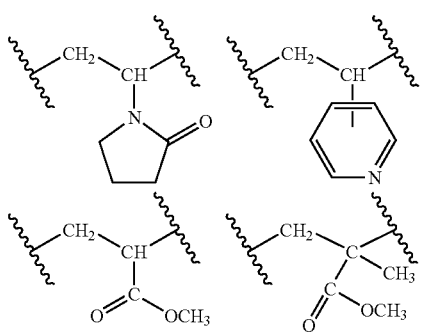

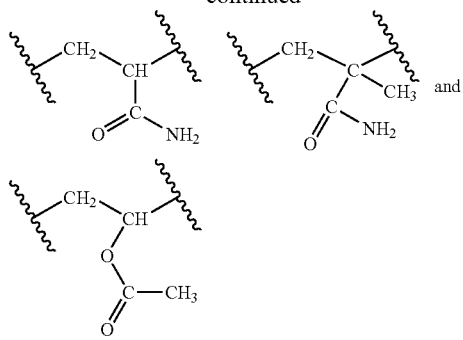

wherein C is A or modified A, wherein modified A is selected from the group consisting of

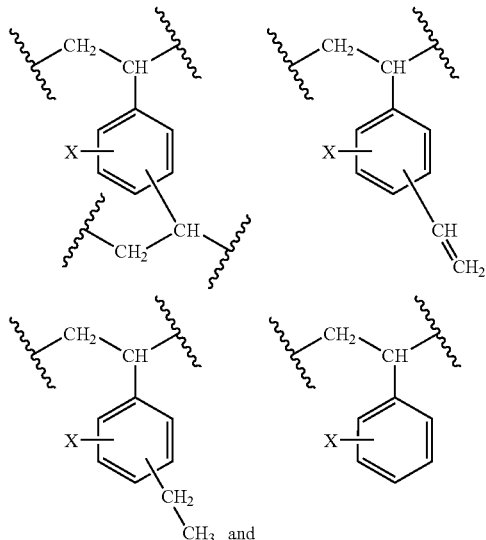

and
wherein X is selected from the group consisting of $SO_3H$, $CH_2CO_2H$, $CH_2CH(CO_2H)_2$, $CO_2H$, $PO_3H_2$, $PO_2H_2$, $CH_2PO_3H_2$, $CH_2Cl$, $CH_2NH_2$, $CH_2N[(CH_2)_yCH_3]_2$ wherein y is any integer from 0 to 18, $CH_2N^+[(CH_2)_{y=}CH_3]_3D^-$ wherein y= is any integer from 0 to 18 and $D^-$ is an anion, $SO_2NHR$ wherein R is polyethylenimine, and $CH_2NHR$ wherein R is polyethylenimine.

Preferred compounds are where X is $SO_3H$, $CH_2PO_3H_2$, $CH_2CO_2H$, or combinations thereof. The most preferred compound is where X is $SO_3H$.

Preferably, X is present at a concentration of about 0.01 to about 5.0, more preferably at a concentration of about 0.6 to about 3.2, more preferably yet at a concentration of about 0.8 to about 2.1, and most preferably at a concentration of about 1.0, milliequivalents per gram of compound.

By block ordering is meant ordering in which individual units are joined in a pattern or repeated sequence. By random ordering is meant ordering in which individual units are joined randomly.

The compounds of this invention can be prepared, e.g., by functionalizing, i.e., chemically altering, a copolymer having at least one hydrophobic monomer, e.g., divinylbenzene, styrene, or ethylvinylbenzene, and at least one hydrophilic monomer, e.g., N-vinylpyrrolidone, N-vinylpyridine, methacrylate, methyl methacrylate, vinyl acetate, acrylamide or methacrylamide. Preferably, the hydrophobic monomer is divinylbenzene. Preferably, the hydrophilic monomer is N-vinylpyrrolidone. The copolymer can be prepared via standard synthetic methods known to those skilled in the art, e.g., as described in Example 1.

Such a copolymer, e.g., poly(divinylbenzene-co-N-vinylpyrrolidone), can be functionalized by the addition of an ion-exchange functional group, an X group, which can be cationic, e.g., $SO_3H$, $CH_2CO_2H$, $CH_2CH(CO_2H)_2$, $CO_2H$, $PO_3H_2$, $PO_2H_2$ or $CH_2PO_3H_2$, or anionic, e.g., $CH_2NH_2$, $CH_2N[(CH_2)_yCH_3]_2$, $CH_2N^+[(CH_2)_{y=}CH_3]_3D^-$, $SO_2NHR$ or $CH_2NHR$, or intermediate, e.g., $CH_2Cl$. Such additions can be accomplished, e.g., as described in Lieto at al., Chemtech, pgs. 46-53 (1983); Mitchell at al., Tetrahedron Letters, pgs. 3795-3798 (1976); and K. Unger, "Packings and Stationary Phases in Chromatographic Techniques," in Chromatographic Science Series, Vol. 47, pgs. 585-720 (1990). See, e.g., Example 2, which describes the sulfonation of poly(divinylbenzene-co-N-vinylpyrrolidone).

The novel compounds of this invention can be used, e.g., as porous resins for solid phase extraction and chromatography. By solid phase extraction is meant a process employing a solid phase for isolating classes of molecular species from fluid phases such as gases and liquids by, e.g., sorption, ion exchange, chelation, size exclusion (molecular filtration), affinity or ion pairing mechanisms.

The invention also includes a porous resin formed by copolymerizing at least one hydrophobic monomer and at least one hydrophilic monomer so as to form a copolymer, and subjecting the copolymer to a sulfonation reaction so as to form a sulfonated copolymer comprising at least one ion-exchange functional group, at least one hydrophilic component and at least one hydrophobic component.

By porous resin is meant a member of a class of crosslinked polymer particles penetrated by channels through which solutions can diffuse. Pores are regions between densely packed polymer chains. By monomer is meant a molecule comprising one or more polymerizable functional groups prior to polymerization, or a repeating unit of a polymer. By copolymer is meant a polymer comprising two or more different monomers. By ion-exchange functional group is meant a group where the counter-ion is partially free and can readily be exchanged for other ions of the same sign. By hydrophilic is meant having an affinity for, attracting, adsorbing or absorbing water. By hydrophobic is meant lacking an affinity for, repelling, or failing to adsorb or absorb water.

In a preferred embodiment, the hydrophobic monomer is divinylbenzene. In a preferred embodiment, the hydrophilic monomer is N-vinylpyrrolidone. In a preferred embodiment, the copolymer is a poly(divinylbenzene-co-N-vinylpyrrolidone). In a preferred embodiment, the porous resin is a sulfonated poly(divinylbenzene-co-N-vinylpyrrolidone). Preferably, the sulfonate groups are present at a concentration of about 0.01 to about 5.0, more preferably at a concentration of about 0.6 to about 3.2, more preferably yet at a concentration of about 0.8 to about 2.1, and most preferably at a concentration of about 1.0, milliequivalents per gram of porous resin.

The invention also includes a porous resin for solid phase extraction or chromatography comprising at least one ion-exchange functional group, at least one hydrophilic component and at least one hydrophobic component.

The ion exchange functional groups enable the porous resin to interact with basic and cationic solutes. The hydrophilic polar components enable the porous resin to have polar interactions and hydrogen bonding capabilities with salutes. The hydrophobic components enable the porous resin to have affinity towards nonpolar solutes through hydrophobic interaction. Since the porous resins of this invention have a combination of various interaction forces towards solutes, they are very useful resins for, e.g., solid phase extraction, ion exchange, liquid chromatography applications. For example, these novel porous resins can be used to bind, recover and/or remove solutes from fluids.

The invention also includes a method for treating a solution to isolate or remove a solute. A solution having a solute is contacted with a porous resin under conditions so as to allow sorption of the solute to the porous resin. The porous resin comprises at least one ion-exchange functional group, at least one hydrophilic polar component and at least one hydrophobic component. In certain embodiments, the solute is removed from the porous resin.

By sorption is meant capable of taking up and holding by absorption or adsorption.

In certain embodiments, the ion-exchange functional group is $SO_3H$, $CH_2CO_2H$, $CH_2CH(CO_2H)_2$, $CO_2H$, $PO_3H_2$, $PO_2H_2$, $CH_2PO_3H_2$, $CH_2Cl$, $CH_2NH_2$, $CH_2N[(CH_2)_yCH_3]_2$ wherein y is any integer from 0 to 18, $CH_2N^+[(CH_2)_{y=}CH_3]_3D^-$ wherein y= is any integer from 0 to 18 and D" is an anion, $SO_2NHR$ wherein R is polyethylenimine, or $CH_2NHR$ wherein R is polyethylenimine. Preferably, the ion-exchange functional group is $SO_3H$. Preferably, the ion-exchange functional groups are present at a concentration of about 0.01 to about 5.0, more preferably at a concentration of about 0.6 to about 3.2, more preferably yet at a concentration of about 0.8 to about 2.1, and most preferably at a concentration of about 1.0, milliequivalents per gram of porous resin.

In certain embodiments, the hydrophilic polar component is an amide group, ester group, carbonate group, carbamate group, urea group, hydroxy group or pyridyl group.

In certain embodiments, the porous resin comprises a copolymer having at least one ion-exchange functional group, and the copolymer comprises at least one hydrophilic monomer and at least one hydrophobic monomer. Preferably, the hydrophilic monomer comprises a heterocyclic group, e.g., a saturated, unsaturated or aromatic heterocyclic group. Examples include nitrogen-containing heterocyclic groups, e.g., a pyridyl group, e.g., 2-vinylpyridine, 3-vinylpyridine or 4-vinylpyridine, or a pyrrolidonyl group, e.g., N-vinylpyrrolidone. Preferably, the hydrophobic monomer comprises an aromatic carbocyclic group, e.g., a phenyl group or a phenylene group, or a straight chain $C_2$-$C_{18}$-alkyl group or a branched chain $C_2$-$C_{18}$-alkyl group. The hydrophobic monomer can be, e.g., styrene or divinylbenzene. A preferred copolymer is a poly(divinylbenzene-co-N-vinylpyrrolidone).

A preferred porous resin is a compound of formula I and salts thereof described supra. Preferably, the porous resin is a sulfonated poly(divinylbenzene-co-N-vinylpyrrolidone).

In preferred embodiments, the porous resin comprises at least about 12 mole percent N-vinylpyrrolidone. In preferred embodiments, the porous resin comprises less than about 30 mole percent N-vinylpyrrolidone. By mole percent is meant the mole fraction, expressed as a percent, of the monomer of interest relative to the total moles of the various (two or more) monomers which compose the copolymer of the porous resin. Preferably, the porous resin has solid phase extraction capability.

The porous resin can be in the form of, e.g., beads, pellets, or any other form desirable for use. The porous resin particles can have, e.g., a spherical shape, a regular shape or an irregular shape. Preferably, the particles are beads having a diameter in the range from about 3 to about 500 μm, preferably from about 20 to about 200 μm. Preferably, the porous resin has a specific surface area in the range from about 50 to about 850 square meters per gram and pores having a diameter ranging from about 0.5 nm to about 100 nm. In certain embodiments, the porous resin is incorporated in a matrix.

In certain embodiments, more than one type of functionalized porous resin can be used in the columns, cartridges, and the like of the present invention.

The solute can be, e.g., any molecule having a hydrophobic, hydrophilic, or ionic interaction or a combination of two or three of these interactions. Preferably, the solute is an organic compound of polarity suitable for adsorption onto the porous resin. Such solutes include, e.g., drugs, pesticides, herbicides, toxins and environmental pollutants, e.g., resulting from the combustion of fossil fuels or other industrial activity, such as metal-organic compounds comprising a heavy metal such mercury, lead or cadmium. The solutes can also be metabolites or degradation products of the foregoing materials. Solutes also include, e.g., biomolecules, such as proteins, peptides, hormones, polynucleotides, vitamins, cofactors, metabolites, lipids and carbohydrates.

The solution e.g., can comprise water, an aqueous solution, or a mixture of water or an aqueous solution and a water-miscible polar organic solvent, e.g., methanol, ethanol, N,N-dimethylformamide, dimethylsulfoxide or acetonitrile. In a preferred embodiment, the solution is an acidic, basic or neutral aqueous, i.e., between about 1% and about 99% water by volume, solution. The solution comprising the solute can, optionally, further contain one or more additional solutes. In one embodiment, the solution is an aqueous solution which includes a complex variety of solutes. Solutions of this type include, e.g., blood, plasma, urine, cerebrospinal fluid, synovial fluid and other biological fluids, including, e.g., extracts of tissues, such as liver tissue, muscle tissue, brain tissue or heart tissue. Such extracts can be, e.g., aqueous extracts or organic extracts which have been dried and subsequently reconstituted in water or in a water/organic mixture. Solutions also include, e.g., ground water, surface water, drinking water or an aqueous or organic extract of an environmental sample, such as a soil sample. Other examples of solutions include a food substance, such as a fruit or vegetable juice or milk or an aqueous or aqueous/organic extract of a food substance, such as fruit, vegetable, cereal or meat. Other solutions include, e.g., natural products extractions from plants and broths.

The solution can be contacted with the porous resin in any fashion which allows sorption of the solute to the porous resin, such as a batch or chromatographic process. For example, the solution can be forced through a porous polymer column, disk or plug, or the solution can be stirred with the porous resin, such as in a batch-stirred reactor. The solution can also be added to a porous resin-containing well of a microtiter plate. The porous resin can take the form of, e.g., beads or pellets. The solution is contacted with the porous resin for a time period sufficient for the solute of interest to substantially sorb onto the porous resin. This period is typically the time necessary for the solute to equilibrate between the porous resin surface and the solution. The sorption or partition of the solute onto the porous resin can be partial or complete.

In one embodiment, the porous resin is packed as particles within an open-ended container to form a solid phase extraction cartridge.

The invention also includes a method for analytically determining the level of solute in a solution. A solution having a solute is contacted with a porous resin under conditions so as to allow sorption of the solute to the porous resin. The resin comprises at least one ion-exchange functional group, at least one hydrophilic polar component and at least one hydrophobic component. The porous resin having the sorbed solute is washed with a solvent under conditions so as to desorb the solute from the porous resin. The level of the desorbed solute present in the solvent after the washing is analytically determined.

In certain embodiments, the porous resin is a compound of formula I and salts thereof. Preferably, the porous resin is a sulfonated poly(divinylbenzene-co-N-vinylpyrrolidone).

The solution contacted with the porous resin can comprise the solute of interest in dilute form, e.g., at a concentration too low for accurate quantitation. By sorbing the solute onto the porous resin and then, e.g., desorbing the solute with a substantially smaller volume of a less polar solvent, a solution which includes the solute of interest can be prepared having a substantially higher concentration of the solute of interest than that of the original solution. The method can also result in solvent exchange, that is, the solute is removed from a first solvent and re-dissolved in a second solvent.

Solvents which are suitable for desorbing the solute from the porous resin can be, e.g., polar water-miscible organic solvents, such as alcohols, e.g., methanol, ethanol or isopropanol, acetonitrile, acetone, and tetrahydrofuran, or mixtures of water and these solvents. The desorbing solvent can also be, e.g., a nonpolar or moderately polar water-immiscible solvent such as dichloromethane, diethylether, chloroform, or ethylacetate. Mixtures of these solvents are also suitable. Preferred solvents or solvent mixtures must be determined for each individual case. A suitable solvent can be determined by one of ordinary skill in the art without undue experimentation, as is routinely done in chromatographic methods development (see, e.g., McDonald and Bouvier, eds., Solid Phase Extraction Applications Guide and Bibliography, "A Resource for Sample Preparation Methods Development," 6th edition, Waters, Milford, Mass. (1995); Snyder and Kirkland, Introduction to Modern Liquid Chromatography, New York: J. Wiley and Sons (1974)).

The level of the desorbed solvent present in the solvent can be analytically determined by a variety of techniques known to those skilled in the art, e.g., high performance liquid chromatography, gas chromatography, gas chromatrography/mass spectrometry, or immunoassay.

The invention also includes a solid phase extraction cartridge comprising a porous resin packed inside an open-ended container. The porous resin comprises at least one ion-exchange functional group, at least one hydrophilic polar component and at least one hydrophobic component. In certain embodiments, the porous resin is a compound of formula I and salts thereof discussed supra. Preferably, the porous resin is a sulfonated poly(divinylbenzene-co-N-vinylpyrrolidone).

The container can be, e.g., a cylindrical container or column which is open at both ends so that the solution can enter the container through one end, contact the porous resin within the container, and exit the container through the other end. The porous resin can be packed within the container as small particles, such as beads having a diameter between about 3 µm and about 500 µm, preferably between about 20 µm and about 200 µm. In certain embodiments, the porous resin particles can be packed in the container enmeshed in a porous membrane.

The container can be formed of any material which is compatible, within the time frame of the solid phase extraction process, with the solutions and solvents to be used in the procedure. Such materials include glass and various plastics, such as high density polyethylene and polypropylene. In one embodiment, the container is cylindrical through most of its length and has a narrow tip at one end. One example of such a container is a syringe barrel. The amount of porous resin within the container is limited by the container volume and can range from about 0.001 g to about 50 kg, and preferably is between about 0.025 g and about 1 g. The amount of porous resin suitable for a given extraction depends upon the amount of solute to be sorbed, the available surface area of the porous resin and the strength of the interaction between the solute and the porous resin. This amount can be readily determined by one of ordinary skill in the art. The cartridge can be a single use cartridge, which is used for the treatment of a single sample and then discarded, or it can be used to treat multiple samples.

The following non-limiting examples further illustrate the present invention.

EXAMPLES

Example 1

Preparation of Poly(Divinylbenzene-co-N-vinylpyrrolidone) Copolymers

This example illustrates the preparation of poly(divinylbenzene-co-N-vinylpyrrolidone) copolymers.

To a 3000 mL flask was added a solution of 5.0 g hydroxypropylmethylcellulose (Methocel E15, Dow Chemical Co., Midland, Mich.) in 1000 mL water. To this was added a solution of 175 g divinylbenzene (DVB HP-80, Dow), 102 g N-vinyl-2-pyrrolidone (International Specialty Products, Wayne, N.J.), and 1.85 g azobisisobutyronitrile (Vazo 64, Dupont Chemical Co., Wilmington, Del.) in 242 g toluene.

The 80% purity divinylbenzene above may be substituted with other hydrophobic monomers such as styrene or ethylvinylbenzene, or lower purity grades of divinylbenzene, but 80% purity divinyl-benzene is preferred. The N-vinylpyrrolidone above may be substituted with other hydrophilic monomers such as N-vinyl-pyridine, methacrylate, methyl methacrylate, vinyl acetate, acrylamide, or methacrylamide, but N-vinylpyrrolidone is preferred.

The resulting biphasic mixture was stirred for 30 minutes at room temperature using sufficient agitation to form oil droplets of the desired micron size. The resulting suspension was then heated under moderate agitation to 70° C. and maintained at this temperature for 20 hours. The suspension was cooled to room temperature, filtered and washed with methanol. The filter cake was then dried in vacuo for 16 hours at 80° C. The composition of the product polymer was determined by elemental analysis. Elemental analysis: N, 2.24%; mole percent N-vinylpyrrolidone: 20%.

A series of poly(divinylbenzene-co-N-vinylpyrrolidone) copolymers comprising about 13, 14, 16, and 22 mole percent N-vinylpyrrolidone was also prepared by this method by varying the starting ratio of the divinylbenzene and N-vinylpyrrolidone monomers.

Example 2

Sulfonation of Poly(divinylbenzene-co-N-vinylpyrrolidone) Copolymers

This example illustrates the preparation of sulfonated poly(divinylbenzene-co-N-vinylpyrrolidone) porous resins. Copolymers obtained from Example 1, preferably poly(divinylbenzene-co-N-vinylpyrrolidone), can be derivatized with sulfuric acid (95-98%, A.C.S. reagent, Aldrich, 25, 810-5, Milwaukee, Wis.). Most preferably, OASIS® HLB (obtained from Waters Corp., Milford, Mass.) is used.

Oasis™ HLB was derivatized with sulfuric acid (95-98%, A.C.S. reagent, Aldrich, 25,810-5, Milwaukee, Wis.). A 1 L, three-necked, round-bottom flask was fitted with a thermometer, agitator, condenser and reactor temperature control system. Sulfuric acid was introduced into the flask (see Table 1 for the amount of sulfuric acid). Then, the agitation and the temperature control were started. The agitator was a ground-glass shaft fitted through the proper Teflon bearing into the center opening atop the flask. The Teflon paddle was single-bladed. The agitation rate was adjusted to ensure adequate mixing. The poly(divinylbenzene-co-N-vinylpyrrolidone), OASIS™ HLB, was charged (see Table 1 for the amount of OASIS™ HLB). The reaction mixture was stirred for a certain period of time at constant temperature (see Table 1 for reaction time and temperature). The reaction mixture was transferred into a 4 L beaker containing 3 L of water. The quenched acid solution was filtered. The sulfonated poly(divinylbenzene-co-N-vinylpyrrolidone) copolymer was collected and washed with 500 ml of water 5 times by filtration. The filter cake of sulfonated poly(divinylbenzene-co-N-vinylpyrrolidone) copolymer was then dried in vacuo for 15 hours at 80° C. The level of sulfonation was determined by sulfur elemental analysis (Atlantic Microlab Inc., Norcross, Ga.). The amount of ion exchange groups ($HSO_3$) on the copolymer is listed in Table 1. Statistical regression analysis results showed that when an excess of sulfuric acid was used, the reaction temperature and reaction time were the main factors influencing the level of sulfonation on the copolymer. Their relationships can be described quantitatively by Equation 1 (R square of 0.996), which can be used for designing sulfonation conditions for preparing copolymers with different ion exchange capacities and which can serve as a guideline for process design and quality control.

Ion exchange capacity of copolymer (meq $HSO_3$/g sulfonated copolymer)=0.53+0.018×[Temperature]+0.00029×[Time],  Equation 1:

wherein
[Temperature]=the reaction temperature in degree celsius.
[Time]=the reaction time in minutes.

TABLE 1

Sulfonated Poly(divinylbenzene-co-N-vinylpyrrolidone) Porous Resins and Respective Reaction Conditions

| Batch No. | Temperature (° C.) | Reaction Time (min) | $H_2SO_4$ (gram) | OASIS ®-HLB (gram) | Sulfonate groups ($HSO_3$) (meq/g) |
|---|---|---|---|---|---|
| JJL03-99 | 25 | 1470 | 250 | 12 | 1.34 |
| JJL03-100 | 100 | 360 | 377 | 15 | 2.52 |
| JJL03-114 | 24 | 70 | 200 | 20 | 1.00 |
| JJL03-115 | 122 | 1380 | 600 | 20 | 3.19 |
| JJL03-119 | 21 | 15 | 200 | 20 | 0.904 |
| JJL03-123 | 122 | 1380 | 800 | 20 | 3.17 |
| JJL03-124 | 22 | 15 | 160 | 20 | 0.898 |
| JJL03-128 | 22 | 75 | 160 | 20 | 1.01 |
| JJL03-129 | 122 | 1380 | 200 | 20 | 3.10 |
| JJL03-138 | 79 | 70 | 800 | 20 | 1.86 |
| JJL03-139 | 83 | 1380 | 200 | 20 | 2.50 |
| JJL03-143 | 0 | 40 | 365 | 20 | 0.602 |

Example 3

Effects of Sulfonation on Chromatographic Retention Behavior of the Sulfonated Resins This example illustrates how the degree of sulfonation of the sulfonated poly(divinylbenzene-co-N-vinylpyrrolidone) resins affected both the hydrophobic and ion-exchange behavior of the resins, as well as the retention properties of the resins.

The resins obtained from Example 2, JJL03-90, 100, 114, 119, 123, 124 and 143, were individually slurry-packed into 4.6×30 mm high performance liquid chromatography (HPLC) columns. The effect of sulfonation on hydrophobic retention and ion-exchange behavior was determined by examining retention of different neutral and basic analytes. The model compounds chosen were: acetaminophen, p-toluamide, caffeine, procainamide, ranitidine, amphetamine, methamphetamine, and m-toluidine. Structures of these model compounds are shown in FIG. 1. The mobile phase consisted of 40:60 methanol—20 mM $(NH_4)H_2PO_4$, pH 3.0 with $NH_4Cl$ as ionic stength modifier. Flow rate was 1.0 mL/min; temperature was 30° C. Injection volume was 5 µL. Each compound was individually injected. Detection was by UV at 254 nm.

Figure 2B:
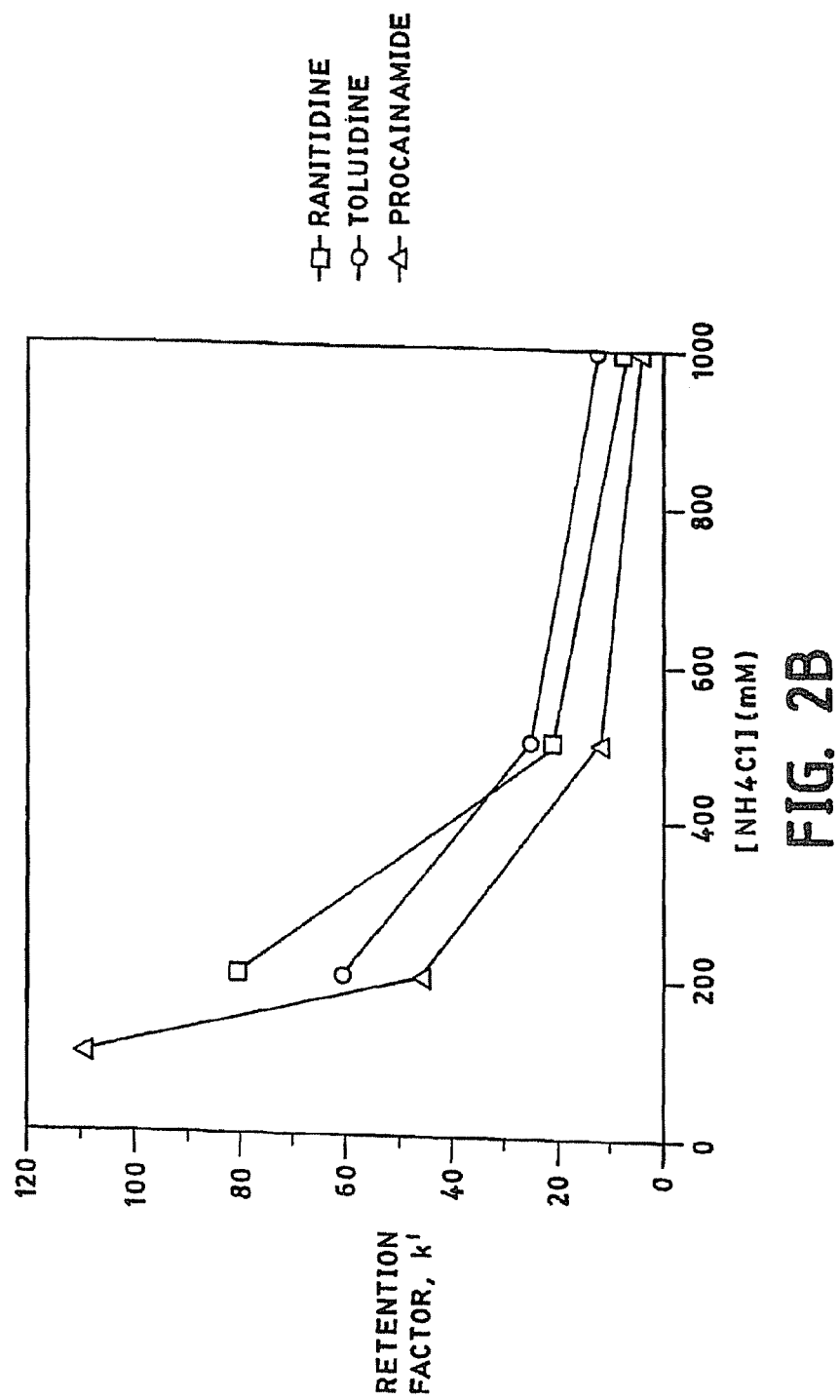
FIGS. 2B and 2C are graphs depicting the effect of ionic strength on chromatographic retention for sulfonated poly(divinylbenzene-co-N-vinylpyrrolidone), Batch JJL03-100.
Figure 2C:
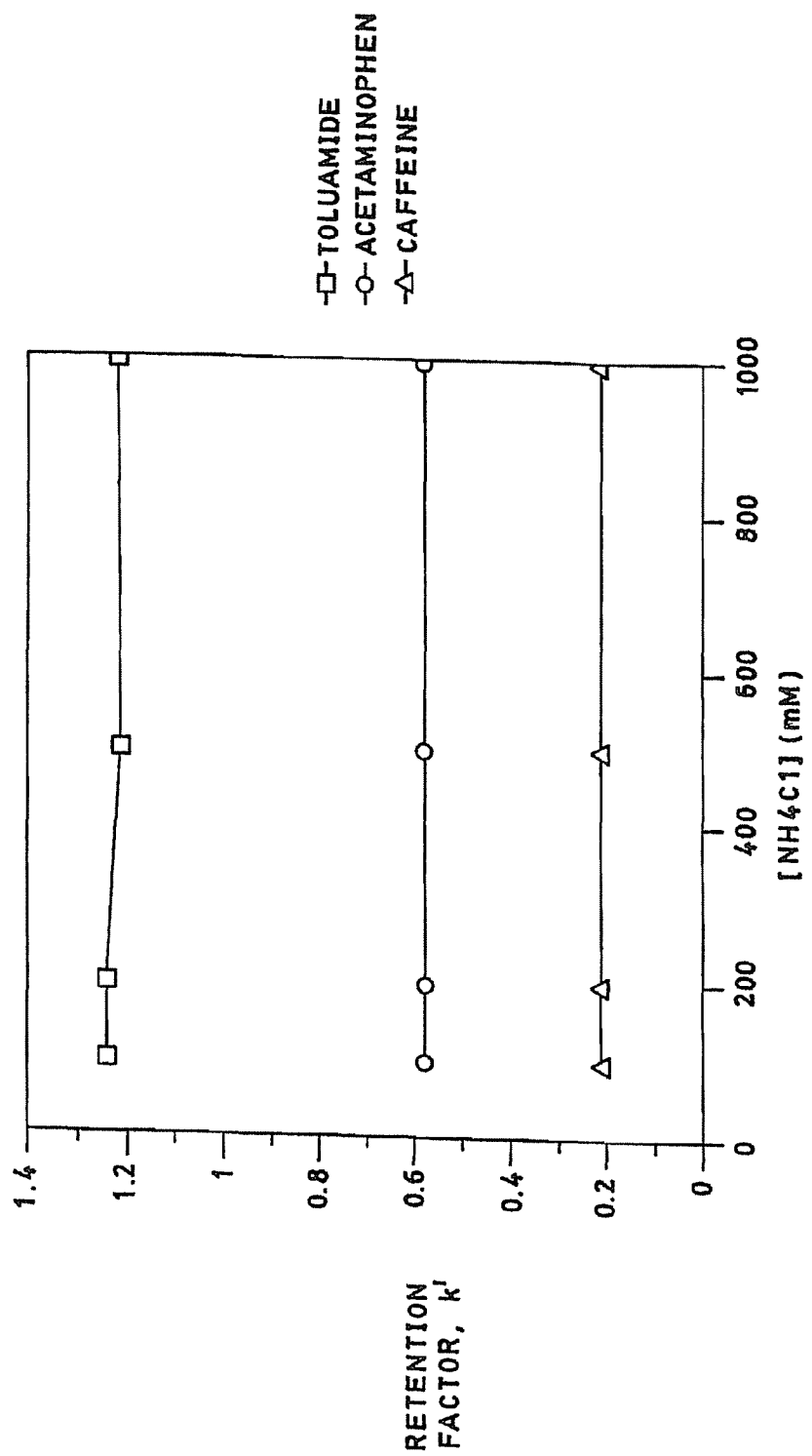

In order to determine whether interactions were by hydrophobic or ionic mechanisms, the retention behavior was determined as a function of ionic strength. FIGS. 2A, 2B, and 2C show the effect of ionic strength on retention for unsulfonated poly(divinylbenzene-co-N-vinylpyrrolidone) (Oasis® HLB, Batch 6B), and for a relatively highly sulfonated poly(divinylbenzene-co-N-vinylpyrrolidone) (Batch JJL03-100) (2.52 meq/g). As can be seen with the unsulfonated resin, there was a very slight increase in retention for all compounds as ionic strength increased. This result is consistent with hydrophobic interaction mechanisms. Also, for the unsulfonated resin, there was only slight hydrophobic retention for the basic compounds under the conditions used, as the retention factor was –<1. In the case of the sulfonated resin, little change in retention for neutral compounds was observed. However, retention of basic compounds was dramatically affected by ionic strength. Retention decreased significantly with increasing ionic strength, indicative of an ion-exchange mechanism.

Figure 4:
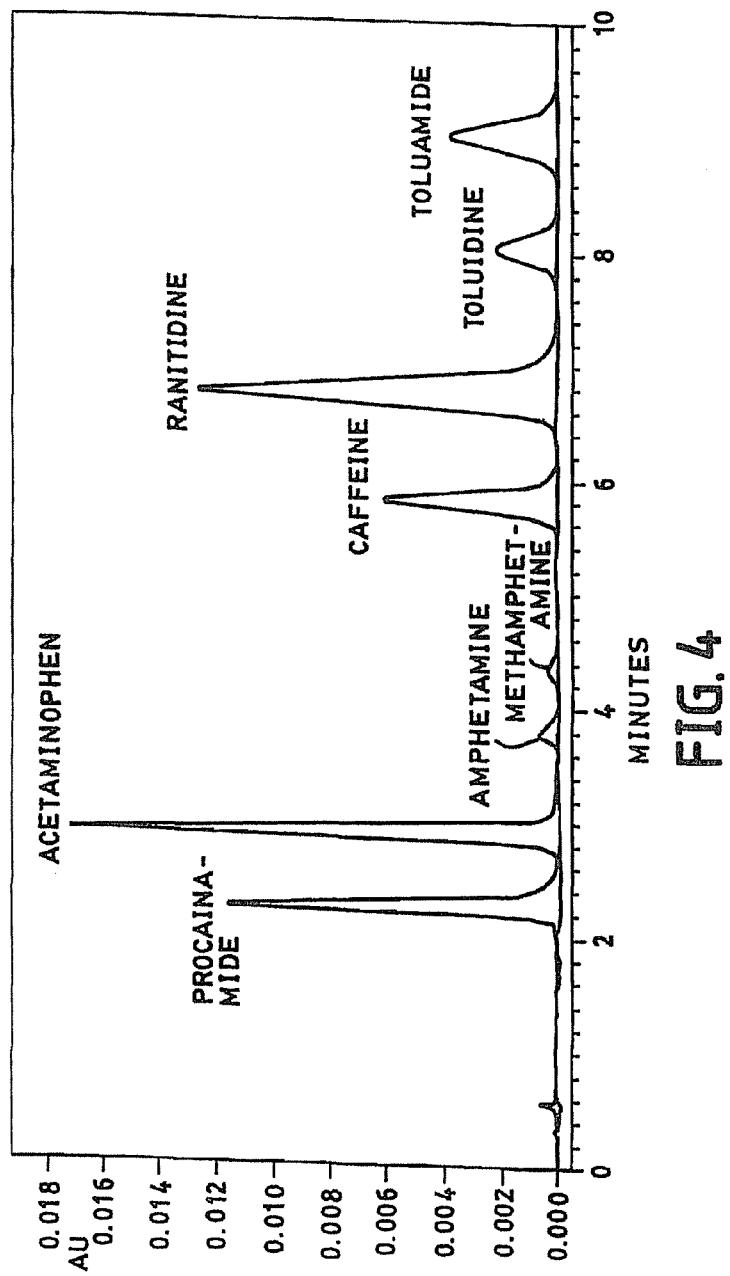
FIG. 4 is a chromatogram depicting separation of model compounds using a SymmetryShield™ $RP_B$ column.

In order to evaluate SPE performance, an HPLC method was developed to examine recovery of several model compounds. A SymmetryShield™ RP8 column, 3.5 µm, 4.6×75 mm (Waters Corp., Milford, Mass.) was used, with a Sentry™ column (Waters Corp., Milford, Mass.) in-line. Flow rate was 2.0 mL/min; temperature was 36° C. Mobile phase consisted of 95:5 20 mM $K_2HPO_4$, pH 7.0—methanol. Detection was by UV at 254 nm. Injection volume was 10 µL. A chromatogram showing the optimized separation is shown in FIG. 4.

For the SPE evaluation, the following resins were used: Oasis® HLB Batch #6B, JJL03-143, JJL03-124 and JJL03-100. SPE was performed using 30 mg of each sorbent in a 96-well plate configuration. The procedure was as follows. The cartridge/well was conditioned with 1 mL methanol (~1 mL/min), and then equilibrated with 1 mL water. A 1 mL sample was loaded which consisted of either spiked phosphate buffered saline, or spiked porcine plasma. Samples were spiked to 10 µg/mL with acetaminophen, toluamide, caffeine and procainamide, and to 20 µg/mL with amphetamine, methamphetamine, and toluidine. The loaded samples were washed with 1 mL of 0.1 M HCl in water, then washed with 1 mL of methanol, and then eluted with 0.5 of 1 mL of methanol containing 2% $NH_4OH$. All fractions after the equilibration were collected. 50 µL of 10 µg/mL ranitidine were added to each sample. The samples were evaporated to dryness under an $N_2$ stream in a heating block. Samples were then reconstituted with 1 mL of 20 mM phosphate buffer, pH 7.0.

Initial SPE performance experiments were done in phosphate-buffered saline. A complete mass balance was performed on SPE fractions using sulfonated poly(divinylbenzene-co-N-vinylpyrrolidone), Batch #JJL03-143. Table 2 shows recovery and mass balance results.

TABLE 2

Recovery and Mass Balance for SPE of Model Compounds from Spiked Phosphate Buffered Saline Using JJL03-143

| JJL03-143 | Load | | Wash (HCl) | | Wash (MeOH) | | Elute ($NH_4OH$, MeOH) | | Elute2 ($NH_4OH$, MeOH) | | Mass bal. |
|---|---|---|---|---|---|---|---|---|---|---|---|
| Compound | Ave | st. dev | Ave | st. dev | Ave | st. dev | Ave | st. dev | Ave | st. dev | Ave |
| Acetaminophen | 0.000 | 0.000 | 0.000 | 0.000 | 0.994 | 0.013 | 0.012 | 0.001 | 0.000 | 0.000 | 1.007 |
| Caffeine | 0.000 | 0.000 | 0.000 | 0.000 | 0.960 | 0.013 | 0.048 | 0.010 | 0.000 | 0.000 | 1.008 |
| Toluamide | 0.000 | 0.000 | 0.000 | 0.000 | 0.974 | 0.010 | 0.000 | 0.000 | 0.000 | 0.000 | 0.974 |
| Procainamide | 0.000 | 0.000 | 0.000 | 0.000 | 0.000 | 0.000 | 0.992 | 0.010 | 0.000 | 0.000 | 0.992 |
| Amphetamine | 0.000 | 0.000 | 0.000 | 0.000 | 0.000 | 0.000 | 0.474 | 0.100 | 0.000 | 0.000 | 0.474 |
| Methamphetamine | 0.000 | 0.000 | 0.000 | 0.000 | 0.000 | 0.000 | 0.428 | 0.108 | 0.000 | 0.000 | 0.428 |
| Toluidine | 0.000 | 0.000 | 0.000 | 0.000 | 0.000 | 0.000 | 0.109 | 0.189 | 0.000 | 0.000 | 0.109 |

Figure 3:
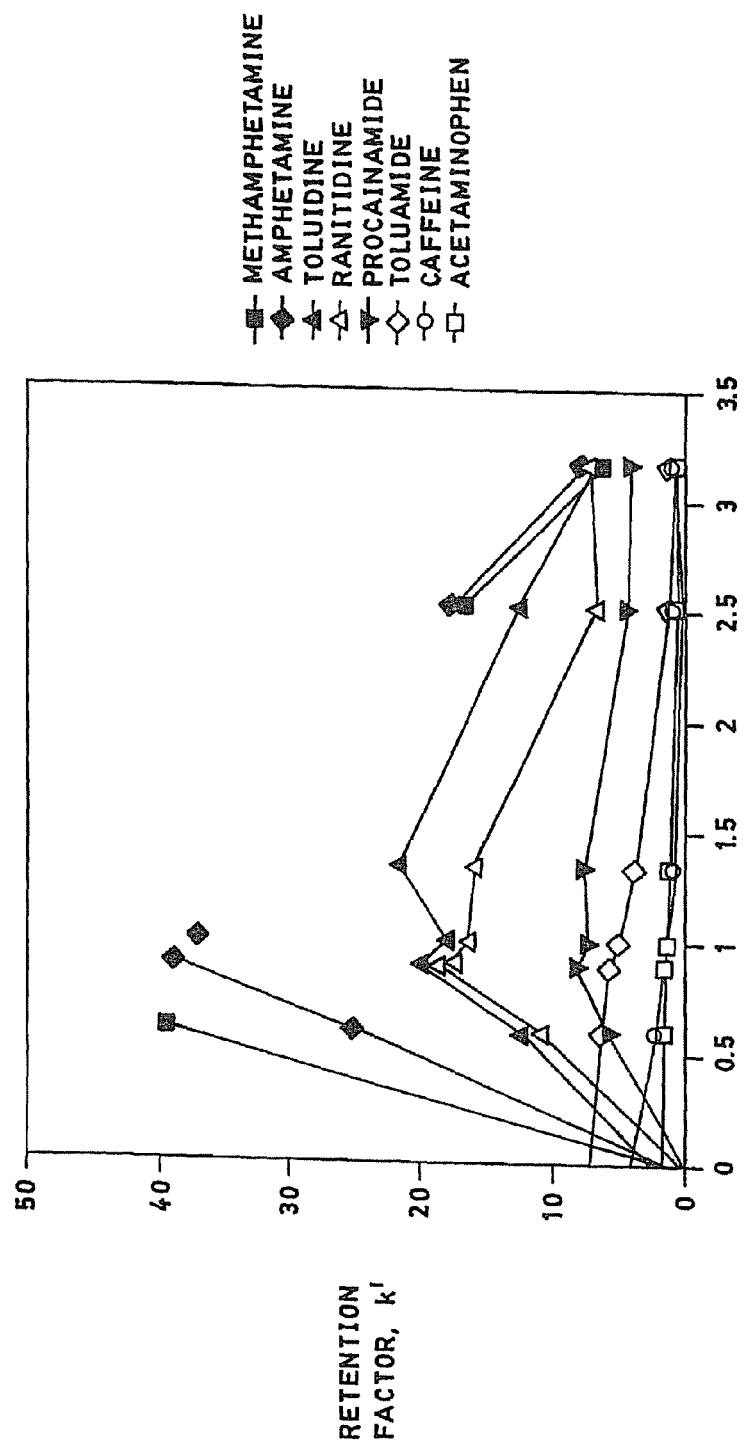
FIG. 3 is a graph depicting the effect of sulfonation on chromatographic retention of model compounds for certain sulfonated resins of this invention.

FIG. 3 shows the effect of sulfonation of the resins on retention. 1M $NH_4Cl$ was used to minimize the retention times. The graph shows that neutral compounds decreased in retention with increasing sulfonation. For the basic compounds, retention increased with increasing sulfonation up to ~1 meq/g. However, at higher levels of sulfonation, retention again decreased.

Example 4

Effects of Sulfonation on Solid Phase Extraction Performance of the Sulfonated Resins This example illustrates the effect of sulfonation of the resins on solid phase extraction (SPE) performance of the sulfonated resins.

Note that amphetamine, methamphetamine and toluidine were not fully recovered in all cases. This was attributed to losses during evaporation, as these compounds are semi-volatile. In experiments where samples were not dried down, complete recovery was obtained. Results from the saline recovery study showed that breakthrough did not occur in the load or HCl wash steps in any case. All compounds eluted in the methanol wash for Oasis® HLB, while only neutral compounds eluted for all the sulfonated resins. Basic compounds could be completely eluted with the methanol/$NH_4OH$ solution. For the sulfonated resin, most of the caffeine eluted in the first methanol wash. In addition, recovery in each fraction was found to depend on the degree of sulfonation; the least sulfonated resins gave greatest recovery in the first methanol wash. This unusual result is attributed to caffeine being a weak base, with a $pK_b$ of 13.9. Another observation was that acetaminophen had a slight amount of breakthrough (~1%) in the methanol/base elution for the sulfonated resins.

Similar results were obtained when using plasma. Table 3 shows results from recoveries obtained on three different sorbents: Oasis® HLB Batch 6B, JJL03-100 and JJL03-124.

TABLE 3

Recovery Results from SPE of Spiked Porcine Plasma (n = 3)

| | Wash (MeOH) | | Elute (MeOH, NH$_4$OH) | | Mass balance |
|---|---|---|---|---|---|
| | Ave. | st. dev. | Ave. | st. dev. | |
| HLB #6B (0.00 meq/g) | | | | | |
| Acetaminophen | 1.009 | 0.021 | 0.000 | 0.000 | 1.009 |
| Caffeine | 0.997 | 0.025 | 0.000 | 0.000 | 0.997 |
| Toluamide | 0.995 | 0.038 | 0.000 | 0.000 | 0.995 |
| Procainamide | 0.239 | 0.002 | 0.038 | 0.005 | 0.277 |
| Amphetamine | 0.825 | 0.103 | 0.000 | 0.000 | 0.825 |
| Methamphetamine | 1.230 | 0.044 | 0.000 | 0.000 | 1.230 |
| Toluidine | 0.569 | 0.037 | 0.000 | 0.000 | 0.569 |
| JJL03-100 (2.52 meq/g) | | | | | |
| Acetaminophen | 0.299 | 0.026 | 0.018 | 0.001 | 0.317 |
| Caffeine | 0.077 | 0.009 | 0.090 | 0.004 | 0.167 |
| Toluamide | 0.823 | 0.011 | 0.053 | 0.007 | 0.876 |
| Procainamide | 0.000 | 0.000 | 0.842 | 0.031 | 0.842 |
| Amphetamine | 0.000 | 0.000 | 0.708 | 0.084 | 0.706 |
| Methamphetamine | 0.000 | 0.000 | 0.732 | 0.180 | 0.732 |
| Toluidine | 0.000 | 0.000 | 0.479 | 0.059 | 0.479 |
| JJL03-124 (0.90 meq/g) | | | | | |
| Acetaminophen | 0.078 | 0.003 | 0.017 | 0.004 | 0.995 |
| Caffeine | 0.901 | 0.058 | 0.083 | 0.054 | 0.984 |
| Toluamide | 0.347 | 0.012 | 0.020 | 0.001 | 0.967 |
| Procainamide | 0.000 | 0.000 | 0.873 | 0.003 | 0.873 |
| Amphetamine | 0.000 | 0.000 | 0.871 | 0.020 | 0.871 |
| Methamphetamine | 0.000 | 0.000 | 0.969 | 0.023 | 0.969 |
| Toluidine | 0.000 | 0.000 | 0.323 | 0.091 | 0.393 |

Figure 5B:
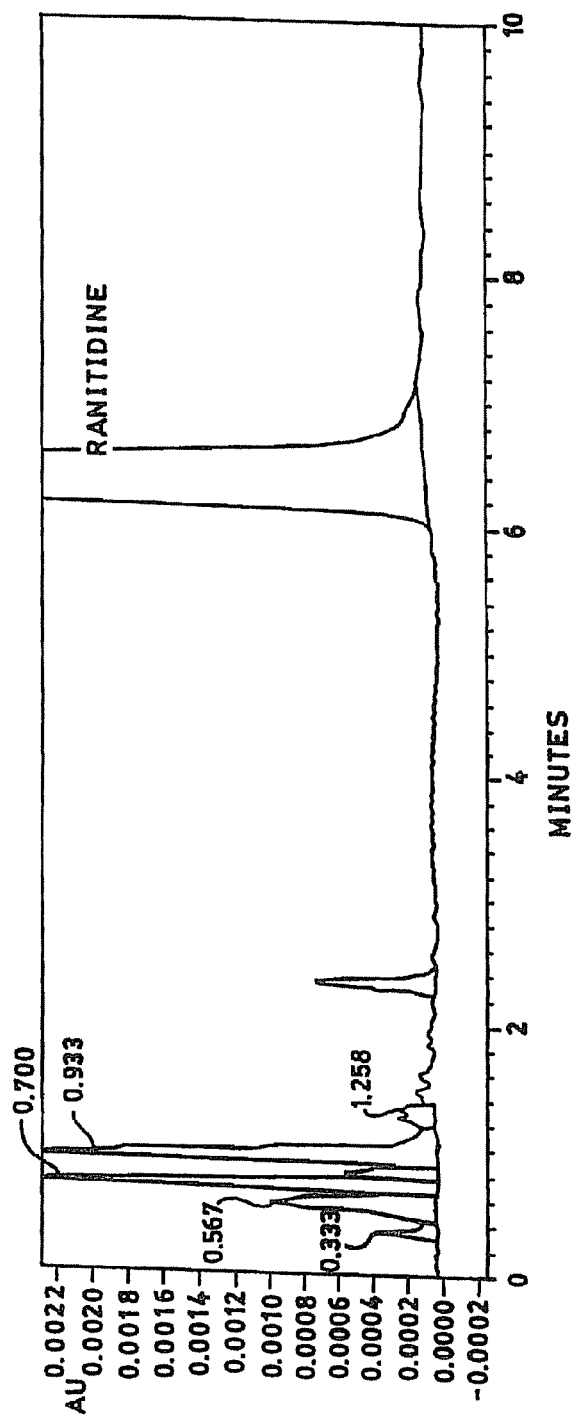

Neutrals eluted in the methanol wash; bases eluted in the methanol/ammonium hydroxide step. HPLC analysis of unspiked plasma extracts from the sulfonated resins are shown in FIGS. 5A and 5B, where ranitidine is an internal standard.

Protein in the extracts was quantitated by Coomassie blue. Two different lots of plasma were tested. Results are shown in Table 4.

TABLE 4

Results from Protein Assay of Methanol/NH$_4$OH Extracts as Determined by Coomassie Blue

| | MeOH/NH4OH Elution Protein Concentration (mg/mL) | |
|---|---|---|
| Sorbent | Plasma Lot #171 | Plasma Lot #180 |
| Oasis ® HLB | 0.012 | 0.012 |
| JJL03-124 | 0.014 | 0.010 |
| JJL03-100 | 0.006 | 0.006 |

Protein in the basified methanol was found to be comparable for Oasis® HLB, JJL03-100 and JJL03-124. As a comparison, these protein amounts were about 5-fold less than what is typically observed using the recommended SPE protocol ("Water Oasis® HLB Extraction Cartridges and Plates," ©1997 Waters Corp., 6/97 WB025-US) for Oasis® HLB cartridges (from the methanol elution step).

At high sulfonation loadings, the plasma load passing through the resin became turbid. A related observation was that the flow rate was found to decrease at high sulfonation loadings. These observations are attributed to the acidity of the resin. The most sulfonated resins have the highest acidity. Thus, passing plasma through the retain was similar to performing an acid precipitation, which makes the sample more turbid, and also can plug up the frit and the packed bed containing the resin.

Example 5

Chloromethylation of poly(divinylbenzene-co-N-vinylpyrrolidone) porous resins

Poly(divinylbenzene-co-N-vinylpyrrolidone), OASIS® HLB, obtained from Waters Corp., Milford, Mass., was derivatized with hydrochloric acid (12 Molar, 36.5-38%, A.C.S. reagent, J. T. Baker, 9535-03, Phillipsburgh, N.J.) and paraformaldehyde (95%, Aldrich Chemical, 15, 812-7, Milwaukee, Wis.). A 3 L, three-necked, round-bottom flask was fitted with a thermometer, agitator, condenser and reactor temperature control system. Hydrochloric acid was introduced into the flask (see Table 5 for the amount of hydrochloric acid). Then, the agitation and the temperature control were started. The agitator was a ground-glass shaft fitted through the proper Teflon bearing into the center opening atop the flask. The Teflon paddle was single-bladed. The agitation rate was adjusted to ensure adequate mixing. The poly(divinylbenzene-co-N-vinylpyrrolidone), OASIS® HLB, was charged (see Table 5 for the amount of OASIS® HLB). Next, the paraformaldehyde was charged (see Table 5 for the amount of paraformaldehyde). The reaction mixture was stirred for a certain period of time at constant temperature (see Table 5 for reaction time and temperature). The reaction mixture was cooled, and the acid solution was filtered. The chloromethylated poly(divinylbenzene-co-N-vinylpyrrolidone) copolymer was collected and washed with water until the pH of the slurry was ≥5.0. The filter cake of chloromethylated poly(divinylbenzene-co-N-vinylpyrrolidone) copolymer was then washed twice with methanol (HPLC grade, J. T. Baker, 9535-03, Phillipsburgh, N.J.) and dried in vacuo for 15 hours at 80° C. The level of chloromethylation was determined by chlorine elemental analysis (Atlantic Microlab Inc., Norcross, Ga.). The loading of chloromethyl groups ($CH_2Cl$) on the copolymer is listed in Table 5.

Reaction time, reaction temperature, and the hydrochloric acid molarity were all found to influence the loading of chloromethyl groups on the poly(divinylbenzene-co-N-vinylpyrrolidone) copolymer. Different combinations of these three variables and the resultant chloromethyl loadings are listed in Table 5.

TABLE 5

Chloromethylated Poly(divinylbenzene-co-N-vinylpyrrolidone) Porous Resins and Respective Reaction Conditions

| Batch No. | Temperature (° C.) | Reaction Time (h) | HCl Molarity | Oasis ® HLB (gram) | HCl (gram) | Paraformaldehyde (gram) | Chloromethyl Loading (meq/g) |
|---|---|---|---|---|---|---|---|
| ARP03-132 | 50 | 1 | 11.1 | 30 | 450 | 17 | 0.61 |
| ARP02-159 | 60 | 16 | 7.5 | 25 | 385 | 14.5 | 0.72 |
| ARP02-98 | 40 | 2 | 12.0 | 16 | 225 | 17 | 0.73 |
| ARP03-132 | 50 | 2 | 11.1 | 30 | 450 | 17 | 0.74 |
| ARP02-92 | 50 | 2 | 12.0 | 16 | 225 | 15 | 0.83 |
| ARP03-132 | 50 | 6 | 11.1 | 30 | 450 | 17 | 0.89 |
| ARP03-132 | 50 | 16 | 11.1 | 30 | 450 | 17 | 1.00 |
| ARP02-161 | 60 | 16 | 9.0 | 25 | 385 | 14.5 | 1.01 |
| ARP03-133 | 70 | 2 | 11.1 | 30 | 450 | 17 | 1.03 |
| ARP02-56 | 60 | 5 | 12.0 | 16 | 250 | 8 | 1.14 |
| ARP02-163 | 60 | 16 | 10.5 | 25 | 385 | 14.5 | 1.15 |
| ARP03-133 | 70 | 16 | 11.1 | 30 | 450 | 17 | 1.23 |
| ARP03-133 | 70 | 6 | 11.1 | 30 | 450 | 17 | 1.24 |
| ARP02-57 | 60 | 25 | 12.0 | 16 | 250 | 8 | 1.35 |
| JJL03-170 | 65 | 21 | 12.0 | 5 | 150 | 8 | 1.38 |
| JJL03-182 | 70 | 25 | 12.0 | 61 | 926 | 51 | 1.43 |

Example 6

Amination of chloromethylated poly(divinylbenzene-co-N-vinylpyrrolidone) porous resins Chloromethylated poly(divinylbenzene-co-N-vinylpyrrolidone) porous resins, prepared as described in Example 5, were reacted with the following tertiary amines (all purchased from Aldrich Chemical, Milwaukee, Wis.): Trimethylamine (TMA, 40 wt. % solution in water, 43,326-8), triethylamine (TEA, 99%, 13,206-3), N,N-dimethylethylamine (DMA, 99%, 23,935-6), N,N-diethylmethylamine (DEMA, 98%, D9,820-3), N,N-dimethylbutylamine (DMBA, 99%, 36,952-7), and N-methylpyrrolidine (NMP, 97%, M7,920-4). A general amination procedure is provided below. The chloromethylation load and the steric size of the reacting amine alkyl groups (see Hirsch, J. A. in *Topics in Stereochemistry, Volume 1*, Allinger, N. L.; Eliel, E. D., Eds. Wiley: New York, 1967, Chapter 1) were found to generally influence the loading of ammonium groups on the poly(divinylbenzene-co-N-vinylpyrrolidone) copolymer. A general reaction procedure is given below. Different combinations of step 1 chloromethyl loading, amine type, and reaction temperature, and the resultant quarternary amine loadings are listed in Table 6.

A 250 mL, three-necked, round-bottom flask was fitted with a thermometer, agitator, condenser and reactor temperature control system. Trialkylamine was introduced into the flask (see Table 6 for the amount of the respective amine), and the agitation and the temperature control were started. The agitator was a ground-glass shaft fitted through the proper Teflon bearing into the center opening atop the flask. The Teflon paddle was single-bladed. The chloromethylated poly (divinylbenzene-co-N-vinylpyrrolidone) was charged (see Table 6 for the amount of resin), and the agitation rate was adjusted to ensure adequate mixing. The reaction mixture was stirred for a certain period of time at constant temperature (see Table 6 for reaction time and temperature). The reaction mixture was cooled, and the amine was filtered. The aminated poly(divinylbenzene-co-N-vinylpyrrolidone) copolymer was collected and washed with water until the pH of the slurry was ≤5.5. The filter cake of aminated poly(divinylbenzene-co-N-vinylpyrrolidone) copolymer was then washed twice with methanol (HPLC grade, J. T. Baker, 9535-03, Phillipsburgh, N.J.) and dried in vacuo for 15 hours at 80° C. The level of amination was determined by titration. The amount of methylenetrialkylammonium groups $(CH_2NR_3^+Cl^-)$ on the copolymer is listed in Table 6.

TABLE 6

Aminated Poly(divinylbenzene-co-N-vinylpyrrolidone) Porous Resins and Respective Reaction Conditions

| Batch No. | Temperature (° C.) | Reaction Time (h) | Chloromethyl resin (gram) | Chloromethyl load (meq/g) | Amine Type | Amine Amount (gram) | Tetraalkylammonium Group Loading (meq/g) |
|---|---|---|---|---|---|---|---|
| ARP-2-153 | 88 | 24 | 50 | 0.76 | TEA | 750 | 0.012 |
| ARP-3-125 | 50 | 3.0 | 12 | 0.74 | DMBA | 50 | 0.030 |
| ARP-2-145 | 85 | 25 | 50 | 1.19 | TEA | 750 | 0.041 |
| JEO-6-65 | 40 | 4.0 | 11 | 1.01 | DMBA | 50 | 0.054 |
| ARP-2-108 | 50 | 25 | 97 | 1.38 | TEA | 388 | 0.067 |
| ARP-2-136 | 40 | 25 | 100 | 0.76 | TMA | 1000 | 0.090 |
| JEO-6-48 | 37 | 19 | 9 | 1.11 | DMEA | 47 | 0.109 |
| JEO-6-47 | 64 | 17 | 9 | 1.11 | DEMA | 47 | 0.114 |
| ARP-3-113 | 50 | 4.0 | 5 | 1.03 | DMBA | 50 | 0.157 |
| ARP-3-139 | 65 | 4.0 | 11 | 1.23 | DMBA | 50 | 0.165 |

TABLE 6-continued

Aminated Poly(divinylbenzene-co-N-vinylpyrrolidone) Porous Resins and Respective Reaction Conditions

| Batch No. | Temperature (° C.) | Reaction Time (h) | Chloro-methyl resin (gram) | Chloro-methyl load (meq/g) | Amine Type | Amine Amount (gram) | Tetraalkylammonium Group Loading (meq/g) |
|---|---|---|---|---|---|---|---|
| JEO-6-43 | 81 | 16 | 8 | 1.11 | NMP | 54 | 0.173 |
| ARP-2-147 | 50 | 5 | 50 | 1.19 | TMA | 500 | 0.184 |
| JEO-6-64 | 85 | 4.0 | 11 | 1.23 | DMBA | 50 | 0.216 |
| ARP-2-115 | 50 | 25 | 5 | 1.42 | TMA | 50 | 0.260 |
| ARP-2-121 | 50 | 25 | 5 | 1.07 | TMA | 50 | 0.290 |
| ARP-3-110 | 93 | 5.0 | 6 | 1.36 | DMBA | 50 | 0.320 |

In conclusion, the experiments demonstrated that sulfonated poly(divinylbenzene-co-N-vinylpyrrolidone) can be used with a generic procedure for SPE of basic compounds. In addition, it can be used as a tool to perform class fractionation of neutral and basic compounds.

Those skilled in the art will be able to ascertain using no more than routine experimentation, many equivalents of the specific embodiments of the invention described herein. These and all other equivalents are intended to be encompassed by the following claims.

What is claimed is:

1. A porous resin for solid phase extraction or chromatography, wherein said porous resin is a compound of formula I:

and salts thereof, wherein the order of A, B and C may be random, block, or a combination of random and block;

wherein $$\frac{1}{100} < \frac{(p+n)}{m} < \frac{100}{1}$$

and $$\frac{1}{500} < \frac{p}{n} < \frac{100}{1};$$

wherein A is selected from the group consisting of

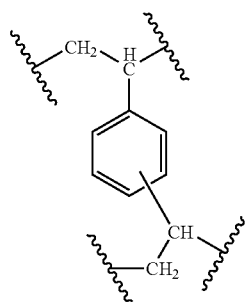 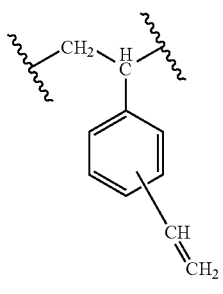

-continued

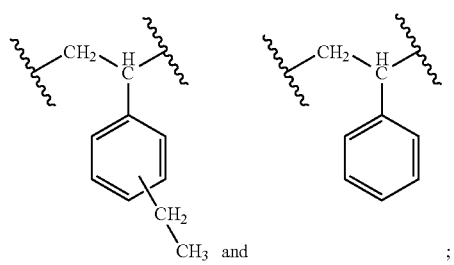

wherein B is selected from the group consisting of

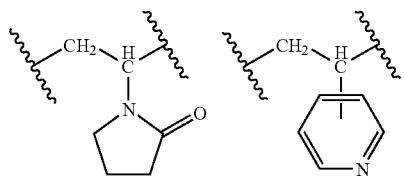

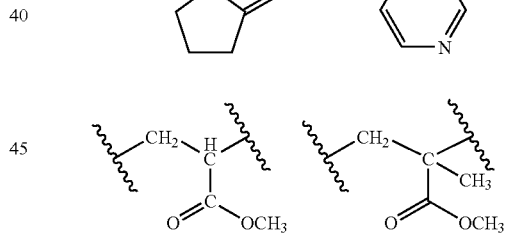

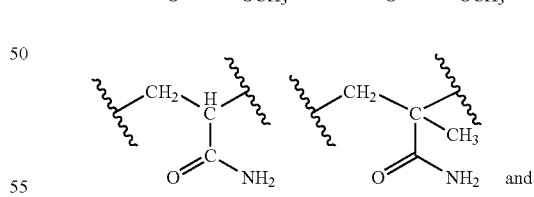 and

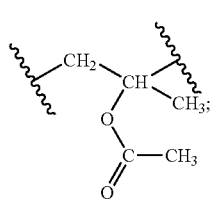

wherein C is A or modified A, wherein modified A is selected from the group consisting of

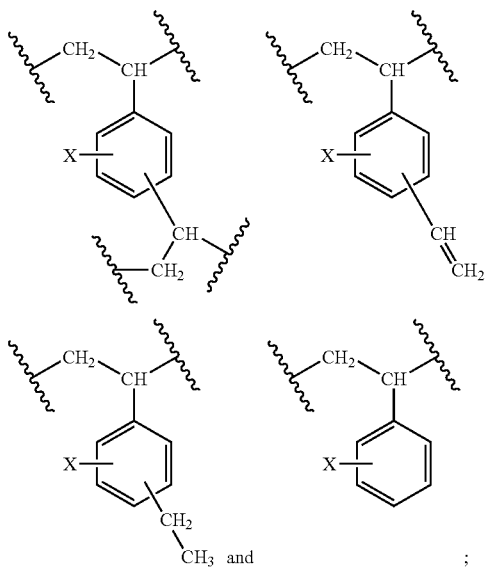

and wherein X is selected from the group consisting of $SO_3H$, $CH_2CO_2H$, $CH_2CH(CO_2H)_2$, $CO_2H$, $PO_3H_2$, $PO_2H_2$, $CH_2PO_3H_2$, $CH_2Cl$, $CH_2NH_2$, $CH_2N[(CH_2)_yCH_3]_2$ wherein y is any integer from 0 to 18, $CH_2N+[(CH_2)_{y'}CH_3]_3D^-$ wherein y' is any integer from 0 to 18 and $D^-$ is an anion, $SO_2NHR$ wherein R is polyethylenimine, and $CH_2NHR$ wherein R is polyethylenimine;

and wherein X is present at a concentration of about 0.6 to about 3.2 milliequivalents per gram of resin.

2. The porous resin of claim 1 wherein X is selected from the group consisting of $SO_3H$, $CH_2PO_3H_2$, and $CH_2CO_2H$.

3. The porous resin of claim 2 wherein X is $SO_3H$.

4. The porous resin of claim 1 wherein B comprises a hydrophilic component is selected from the group consisting of an amide group, ester group, carbonate group, carbamate group, urea group, hydroxy group and pyridyl group.

5. The porous resin of claim 1, wherein B comprises a heterocyclic group.

6. The porous resin of claim 5 wherein said heterocyclic group is a pyridyl group or a pyrrolidonyl group.

7. The porous resin of claim 6 wherein said pyridyl group is selected from the group consisting of 2-vinylpyridine, 3-vinylpyridine and 4-vinylpyridine.

8. The porous resin of claim 6 wherein said pyrrolidonyl group is N-vinylpyrrolidone.

9. The porous resin of claim 1, wherein A comprises a group selected from the group consisting of a phenyl group, a phenylene group, a straight chain $C_2$-$C_{18}$-alkyl group and a branched chain $C_2$-$C_{18}$-alkyl group.

10. The porous resin of claim 1, wherein said porous resin is a poly (divinylbenzene-co-N-vinylpyrrolidone).

11. The porous resin of claim 1, wherein said porous resin is a sulfonated poly (divinylbenzene-co-N-vinylpyrrolidone).

12. The porous resin of claim 1, wherein said porous resin is in the form of a bead.

* * * * *